US012659710B2

(12) United States Patent
Haygood et al.

(10) Patent No.: US 12,659,710 B2
(45) Date of Patent: Jun. 16, 2026

(54) TELEHEALTH SYSTEM FOR PROVIDING REAL-TIME DETECTION AND PROCESSING OF EMERGENCY COMMUNICATIONS

(71) Applicants: June Haygood, Stonecrest, GA (US); Jayfus Tucker Doswell, Baltimore, MD (US)

(72) Inventors: June Haygood, Stonecrest, GA (US); Jayfus Tucker Doswell, Baltimore, MD (US)

( * ) Notice: Subject to any disclaimer, the term of this patent is extended or adjusted under 35 U.S.C. 154(b) by 543 days.

(21) Appl. No.: 17/737,001

(22) Filed: May 4, 2022

(65) Prior Publication Data

US 2023/0362611 A1      Nov. 9, 2023

(51) Int. Cl.
  *H04W 4/90*         (2018.01)
  *G16H 80/00*        (2018.01)
  *H04W 4/02*         (2018.01)

(52) U.S. Cl.
  CPC .............. *H04W 4/90* (2018.02); *G16H 80/00* (2018.01); *H04W 4/023* (2013.01); *H04W 4/025* (2013.01)

(58) Field of Classification Search
  CPC ....... H04W 4/90; H04W 4/023; H04W 4/025; H04W 4/02; H04W 4/06; G16H 80/00; G16H 40/20; G16H 50/20; G16H 50/30
  See application file for complete search history.

(56) References Cited

U.S. PATENT DOCUMENTS

| | | | | |
|---|---|---|---|---|
| 9,794,755 | B1 * | 10/2017 | South .................... | H04W 4/021 |
| 2012/0252398 | A1 * | 10/2012 | Jacobs ............... | H04B 7/15507 |
| | | | | 455/404.1 |
| 2018/0199179 | A1 * | 7/2018 | Rauner .................. | G08B 25/10 |

* cited by examiner

*Primary Examiner* — Kabir A Timory
(74) *Attorney, Agent, or Firm* — Kimberly McLean

(57)            ABSTRACT

A system and method for detecting and processing emergency communications in real-time using an emergency communication management enterprise system. The real-time emergency communication detection and processing includes receiving an emergency alert from a requesting client device, automatically tracking the geographic coordinates of the requesting client device, performing a proximity analysis to identify an affiliate client device within a predetermined distance of the requesting client device, and broadcasting an emergency notification to the affiliate client device within the predetermined distance of the requesting client device.

20 Claims, 4 Drawing Sheets

160

100

160

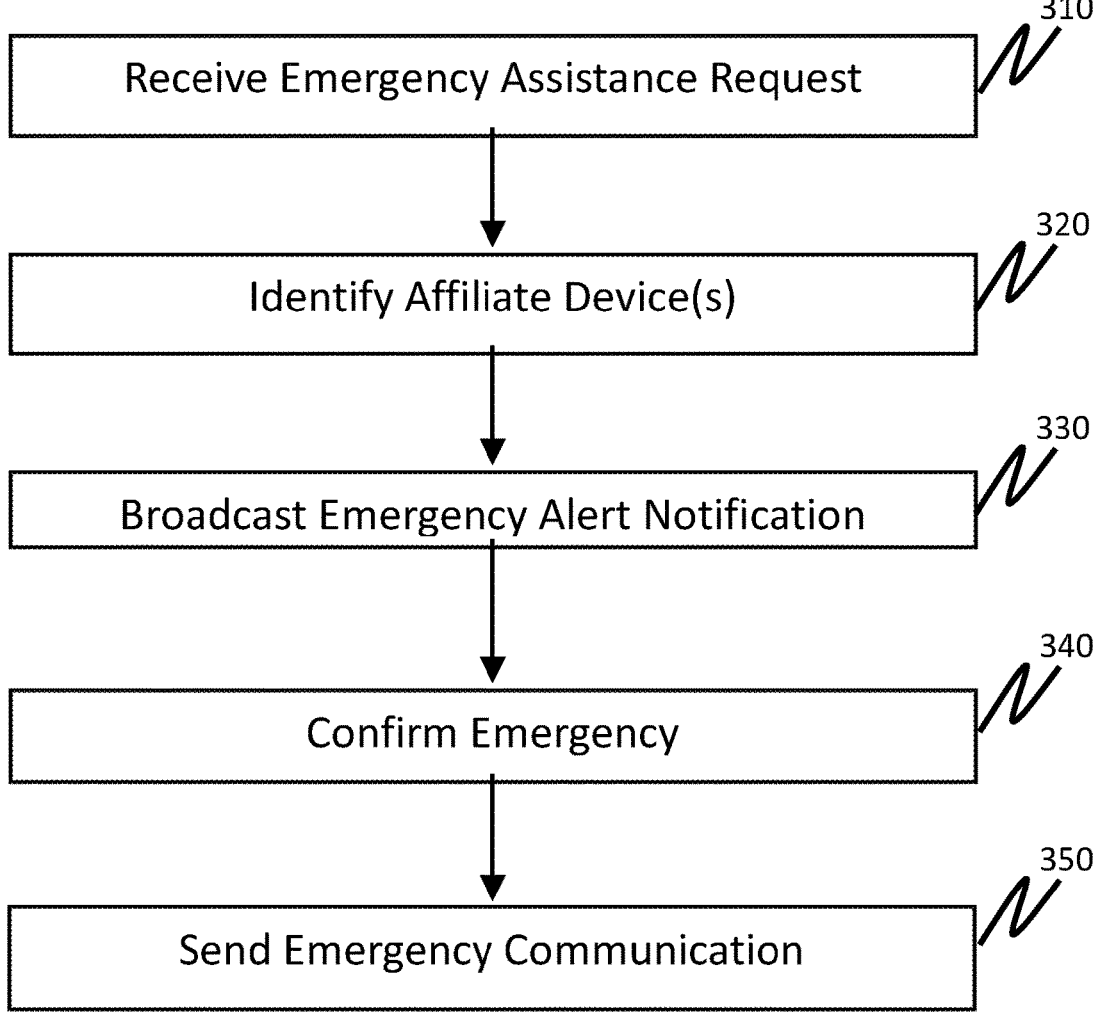
310
Receive Emergency Assistance Request
320
Identify Affiliate Device(s)
330
Broadcast Emergency Alert Notification
340
Confirm Emergency
350
Send Emergency Communication
300          FIG. 3

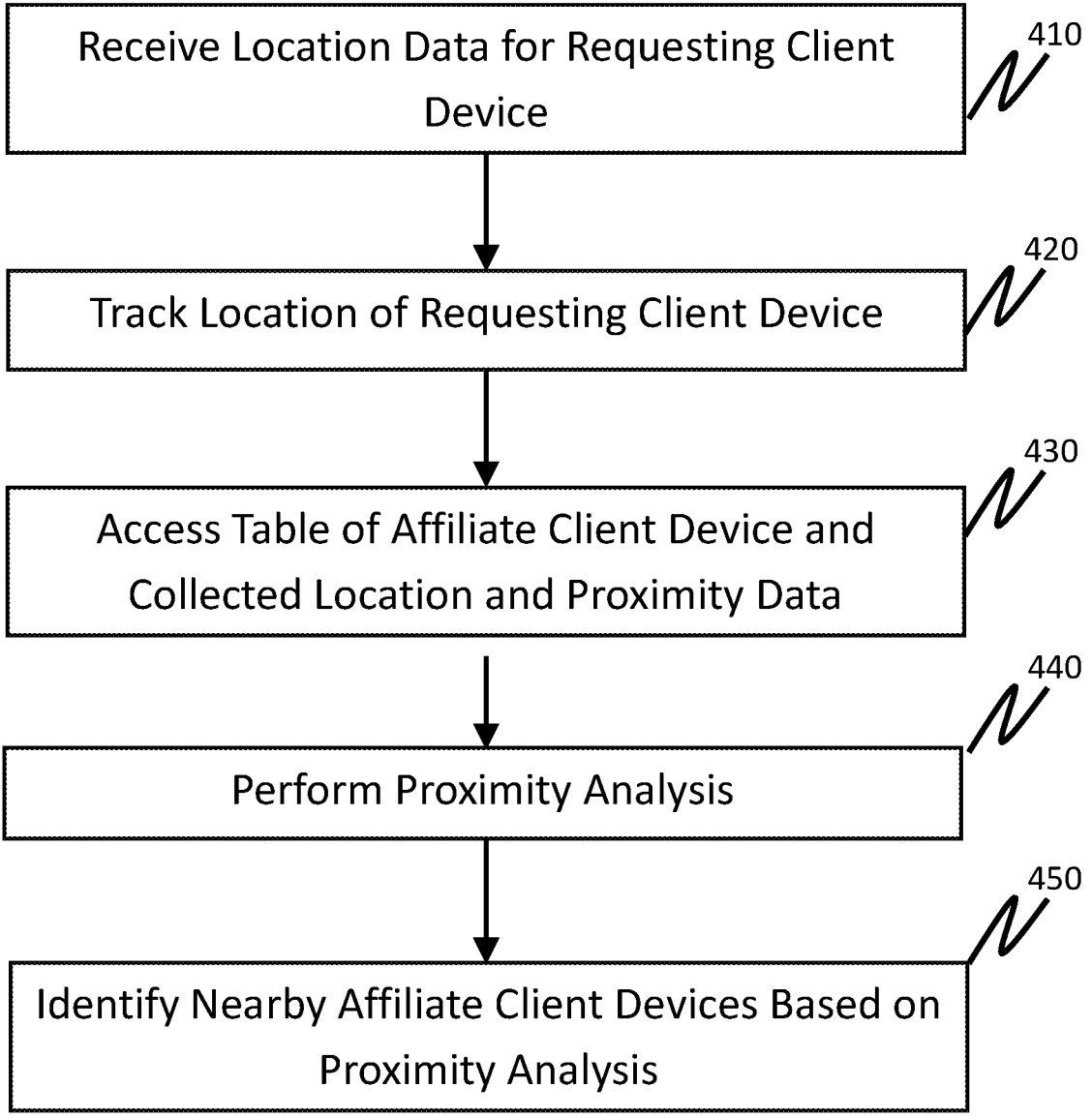
Receive Location Data for Requesting Client Device            410
Track Location of Requesting Client Device            420
Access Table of Affiliate Client Device and Collected Location and Proximity Data            430
Perform Proximity Analysis            440
Identify Nearby Affiliate Client Devices Based on Proximity Analysis            450
400                    FIG. 4

TELEHEALTH SYSTEM FOR PROVIDING REAL-TIME DETECTION AND PROCESSING OF EMERGENCY COMMUNICATIONS

FIELD OF THE INVENTION

Embodiments described herein generally relate to processing emergency communications, and more particularly to a telehealth system for providing real-time detecting and processing of emergency communications.

BACKGROUND OF THE INVENTION

Greater than 46,802 Americans died of opioid overdose in 2018 with 130 daily deaths and one person dead every 12.5 minutes. Researchers state that if prescription opioid misuse rates remain unchanged, an estimated 700,400 people will die from opioid overdose in 2025. 80% of those deaths would be attributed to illicit opioids such as heroin or fentanyl. Millions of Americans report addiction to opioids or Opioid Use Disorder (OUD) resulting in ~$78.5 billion economic burden of prescription opioid misuse, in the United States (U.S.).

Without timely reversal, opioid overdose causes respiratory depression that may deteriorate into apnea, leading to anoxic injury, brain damage (i.e., in less than five minutes), and death. Each minute of cerebral ischemia is associated with potential irreversible brain damage. Hence, timely reversal requires fast on-scene arrival; accurate overdose identification; and fast/accurate naloxone administration. However, oftentimes EMTs or paramedics arrive to an opioid overdose scene between 10 and 16 minutes after a bystander has identified the overdose; a time-frame too long to administer life-saving care when brain damage can rapidly occur.

In many other medical emergency situations, a distressed party will need to receive assistance from a trained provider, such as, for example, a first responder. In time-sensitive medical emergencies, fast treatment can make a big difference in the eventual outcome for the distressed party. Conditions, such as, heart attacks, seizures, drug overdoses, strokes and severe trauma are considered time-sensitive medical emergencies. Oftentimes, a trained provider is not located in real-time where the distressed party is having a medical emergency, and thus, the distressed party will have to wait a period of time before the arrival of the trained provider. Hence, it could be extremely beneficial if the distressed party were able to obtain some level of assistance while waiting for the trained provider. Nowadays, mobile devices are widely used and are considered to be a necessity for many people. It's a powerful communication device that can be used to aid a distressed party in real-time in an emergency situation.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably. The various advantages of the embodiments of the present disclosure will become apparent to one skilled in the art by reading the following specification and appended claims, and by referencing the following drawing(s), in which:

FIG. 3 shows an exemplary high level flow diagram of a method for real-time detection and processing of emergency communications according to an embodiment of the present disclosure.

FIG. 4 shows an exemplary high level flow diagram of a method for identifying a client device within a predetermined distance of a requesting client device according to an embodiment of the present disclosure.

SUMMARY OF THE INVENTION

Figure 1:
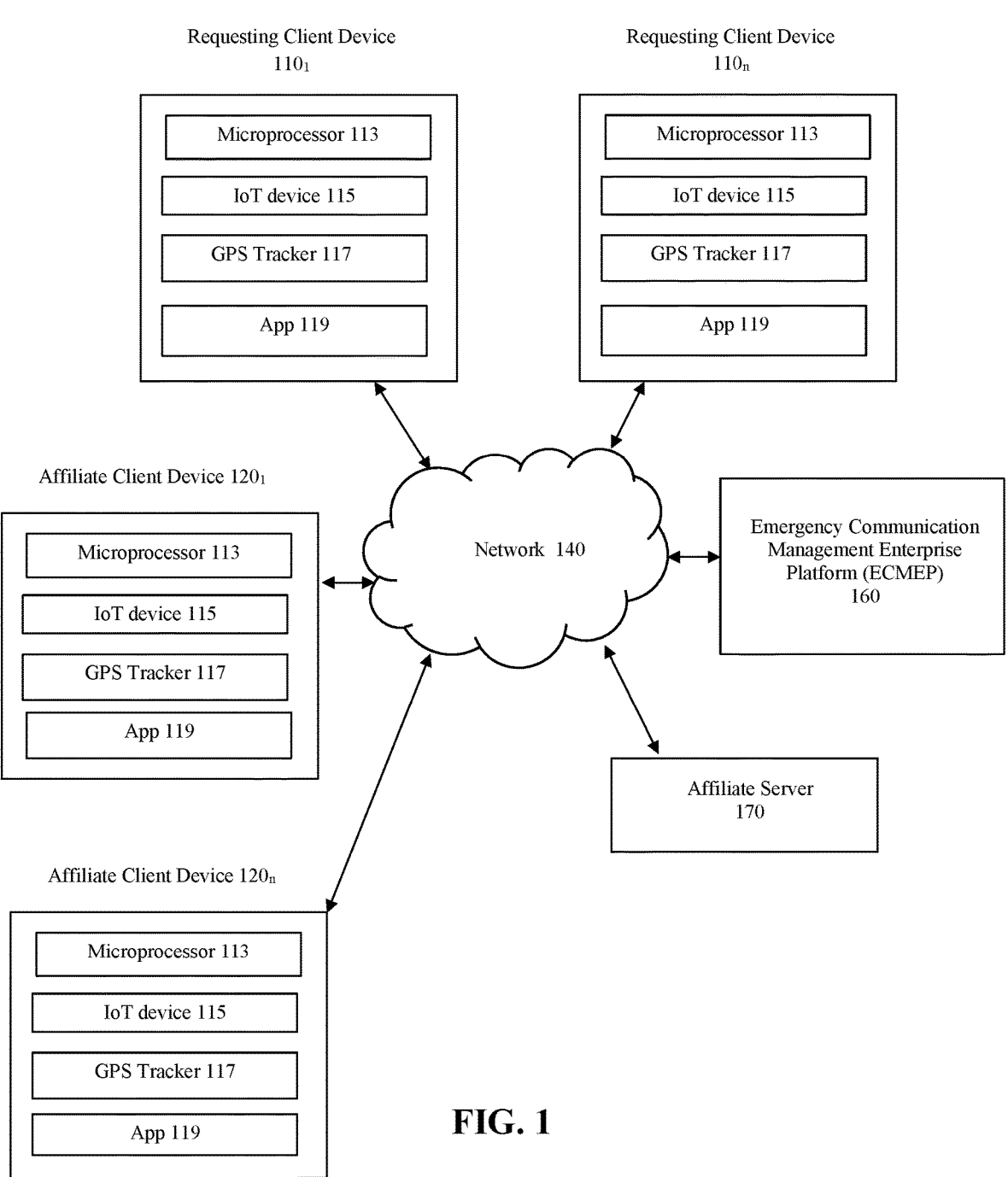
FIG. 1 depicts an illustrative architecture in which techniques and structures for providing the systems and methods disclosed herein may be implemented.

Exemplary embodiments disclosed herein describe a computer implemented method of real-time detection and processing of emergency communications. The method comprising the steps of: receiving an emergency assistance request from a requesting client device; automatically tracking the geographic coordinates of the requesting client device; performing a proximity analysis to identify at least one affiliate client device within a predetermined distance of the requesting client device upon receipt of the emergency assistance request; broadcasting an emergency notification to the at least one affiliate client device within the predetermined distance of the requesting client device.

In some exemplary embodiments, the method further includes the step of transmitting an emergency notification to an affiliate server upon receipt of the emergency assistance request.

In some exemplary embodiments, the method further includes the step of creating a table including a list of affiliate client devices.

In some exemplary embodiments, the method further includes the step of continuously collecting location data from the list of affiliate client devices.

In some exemplary embodiments, the location data includes proximity beacon sensor data.

In some exemplary embodiments, the location data includes Wi-Fi access points data.

In some exemplary embodiments, the performed proximity analysis includes short range proximity detection between the requesting client and the at least one affiliate client device.

In some exemplary embodiments, the method further includes the step of performing diagnosis analytics on information received from an affiliate client device to confirm the emergency.

In some exemplary embodiments, the method further includes the step of transmitting an emergency communication to the affiliate client device upon confirmation of the emergency.

Other exemplary embodiments disclosed herein describe a system for real-time detection and processing of emergency communications. The system includes at least one a client interface unit for interfacing with at least one client device; at least one data storage device including a first database for storing a list of affiliate client devices; an Internet of things (IoT) interface unit for interfacing with at least one IoT device; at least one processor; at least one memory for storing executable instructions, the at least one processor configured to execute the instructions to: receive an emergency assistance request from a requesting client device; automatically track the geographic coordinates of the requesting client device; perform a proximity analysis to identify at least one affiliate client device within a predetermined distance of the requesting client device upon receipt of the emergency alert; and broadcast an emergency notification to the at least one affiliate client device within the predetermined distance of the requesting client device.

Further, the system includes a first network interface configured to transmit an emergency assistance request to an affiliate server.

Further, the system includes a second network interface configured to continuously collect location data from the list of affiliate client devices.

Further, the system includes a machine learning module including at least one processor configured to execute computer executable instructions to: perform diagnosis analytics on information received from an affiliate client device using at least one machine learning algorithm to confirm an emergency.

Further, the system includes a third network interface for transmitting an emergency communication to a the affiliate client device upon confirmation of the emergency.

In some exemplary embodiments, the performed proximity analysis includes short range proximity detection between the requesting client and the at least one affiliate client device.

Other exemplary embodiments disclosed herein describe a non-transitory computer readable medium comprising instructions, that when read by a processor, cause the processor to perform: receive an emergency assistance request from a requesting client device; automatically track the geographic coordinates of the requesting client device; perform a proximity analysis to identify at least one affiliate client device within a predetermined distance of the requesting client device upon receipt of the emergency alert; and broadcast an emergency notification to the at least one affiliate client device within the predetermined distance of the requesting client device.

Further, the non-transitory computer readable medium comprises instructions, that when read by the processor, cause the processor to create a table including a list of affiliate client devices.

Further, the non-transitory computer readable medium comprises instructions, that when read by the processor, cause the processor to continuously collect location data from the list of affiliate client devices.

Further, the non-transitory computer readable medium comprises instructions, that when read by the processor, cause the processor to perform diagnosis analytics on information received from an affiliate client device to confirm an emergency.

Further, the non-transitory computer readable medium comprises instructions, that when read by the processor, cause the processor to transmit an emergency communication to the affiliate client device based on the confirmed emergency.

DETAILED DESCRIPTION

The disclosure will be described more fully hereinafter with reference to the accompanying drawings, in which exemplary embodiments of the disclosure are shown. This disclosure may, however, be embodied in many different forms and should not be construed as limited to the exemplary embodiments set forth herein. It will be apparent to persons skilled in the relevant art that various changes in form and detail can be made to various embodiments without departing from the spirit and scope of the present disclosure. Thus, the breadth and scope of the present disclosure should not be limited by any of the above-described exemplary embodiments but should be defined only in accordance with the following claims and their equivalents.

Turning now to the drawings, FIG. 1 depicts an illustrative architecture 100 in which techniques and structures of the present disclosure may be implemented. The illustrative architecture 100 may include at least one requesting client device 110, at least one affiliate client device 120, a network 140, at least one emergency communication management enterprise platform (ECMEP) 160 and at least one affiliate server 170. The requesting client device 110 and the affiliate client device 120 may be collectively referred to as client device 110, 120.

Although not shown, the illustrative architecture 100 may include one or more electronic communication channels for transmitting data between requesting client device 110, affiliate client device 120, network 140, emergency communication management enterprise platform 160 and affiliate server 170. While a limited number of requesting client devices 110, affiliate client devices 120, networks 140, emergency communication management enterprise platform 160 and affiliate servers 170 are illustrated, the architecture 100 may include any number of requesting client devices 110, affiliate client devices 120, networks 140, emergency communication management enterprise platform 160 and affiliate servers.

The network 140 may include any one or a combination of multiple different types of networks, such as cable networks, the Internet, wireless networks, and other private and/or public networks. In some instances, the network 140 may include cellular, Wi-Fi, or Wi-Fi direct. The network may be the Internet or any other suitable network for the transmitting of data from a source to a destination.

The at least one requesting client device 110 and the at least one affiliate client device 120 may include a mobile device, a tablet, a laptop device, a wearable device (e.g., augmented reality goggles or smart wrist band), a remote camera system, and/or a personal desktop computer. The client device (i.e., the at least one requesting client device 110 and the at least one affiliate client device 120) is communicably coupled to the network 140. It should be noted that other types of devices might be used with the present application. For example, a PDA, an MP3 player, or any other wireless device, a gaming device (such as a handheld system or home based system), any computer wearable device, and the like (including a P.C. or other wired device) that may transmit and receive information may be used with the present application.

The client device (110, 120) may execute a user browser used to interface with network 140, an email application used to send and receive emails, a text application used to send and receive text messages, and many other types of applications. Communication may occur between the client device and the network 140 via applications (e.g., app 119) executing on the client device (i.e., 110, 120) and the applications may be downloaded via an application store or may reside on the client device by default. Additionally, communication may occur on the client device using the client device's operating system to perform the logic to communicate without the use of applications. The client device (110, 120) may include one or more user interfaces (e.g., voice user interface, graphical user interface, touch user interface, etc.).

The client device (110, 120) may include one or more computer-readable storage media, one or more processors (e.g., 113) and one or more computer programs (e.g., 119). One or more of the computer programs may include code that is used to execute a telehealth emergency assistance platform ("TEAP")(e.g., application 119). The telehealth emergency assistance platform may include one or more processors and one or more computer programs. The telehealth emergency assistance platform may operate (i.e., run/execute) on a client device (110, 120) and the platform may include any one or more from the group comprising a web site, web browser, application programming interfaces, operating system, web application, cloud application, mobile application, and social media site. The telehealth emergency platform may include one or more user interfaces (e.g., voice user interface, graphical user interface, touch user interface, etc.) which allow the TEAP to send and receive data to an end user (e.g., requesting user, affiliate user, payer user). The telehealth emergency assistance platform may include a back-end processing system (i.e., emergency communication management enterprise platform (ECMEP) 160).

The telehealth emergency assistance platform (TEAP) includes at least one user interface which allows a user to request emergency assistance ("requesting user"). In some aspects the requesting user may be a bystander, an individual not trained to provide emergency assistance to an injured/distressed individual. In other aspects, the requesting user may be a wearable device (e.g., a wristband) worn by the injured/distressed individual. The wearable device may include one or more sensors which are configured to detect when a morbidity is occurring to the individual wearing the wearable device, and once such a detection is made, the wearable device may interface with the TEAP and send an emergency assistance request. In other aspects, the requesting user may be a remote camera or a mobile camera. Each camera may include computer vision facial and body recognition, which may be used to detect when a morbidity is occurring to an individual, and once such a detection is made, each camera may interface with the TEAP and send an emergency assistance request.

In some aspects, the TEAP includes at least one user interface which allows a user ("payer") to make financial contributions using the platform to cover the expenses for the services provided and the drugs provided as services of the TEAP.

When the TEAP receives the emergency assistance request, the ECMEP 160 will identify one or more affiliate client devices 120 within a predetermined distance of the requesting device 110 and broadcast an emergency alert notification to the identified one or more identified affiliate client devices 120. In some aspects, the ECMEP may send an emergency notification to affiliate server 170.

Upon receiving an acceptance confirmation from at least one of the identified affiliate client devices, the ECMEP will send the location of the requesting user to the at least one identified affiliate client device 120. When the at least one affiliate client device arrives to the location, the client device 120 will send an arrival notification to the ECMEP. Thereafter, the ECMEP confirms the emergency using data captured by the confirming affiliate client device (i.e., the affiliate client device that sent the acceptance confirmation), and upon confirmation of the emergency, the ECMEP will send an emergency communication (e.g., the steps to administer aid to the distressed individual) to the at least one affiliate client device.

In some aspects, the TEAP may provide information about the closest available location to get a drug (e.g., naloxone). Moreover, in some aspects, the TEAP may facilitate a bi-directional video-conference between an affiliate user using an affiliate client device (e.g., AR Goggles) and organization affiliated with affiliate server 170 (e.g., 911 dispatched & arriving EMT/Paramedics).

Further, each client device (110,120) may include at least one internet of things (IoT) device 115, at least one global positioning system (GPS) tracker 117 and at least one app 119. The IoT device may include, for example, a proximity beacon, Bluetooth beacon, sensor, etc. The IoT device 115 may be capable of interacting and communicating with each other and/or with other devices (e.g., 110, 120, 140, 160 and 170) connected to network 140 over various wireless communication standards (e.g., Wi-Fi, Zigbee, Bluetooth, etc.) or wired communication standards (e.g., Ethernet, Multimedia over Coax Alliance (MoCA), etc.).

Each IoT device 115 may include a user IoT interface (e.g., a web app, mobile app, remote control, display screen integrated within the device itself, voice activation interface), one or more sensors and/or actuators, a network interface, and at least one embedded microcontroller (e.g., a small ARM computer with firmware and a Bluetooth Smart connectivity module, which is powered by a battery). The user IoT interface allows a user to interact with a corresponding IoT device 115 and/or client device 110, 120, to collect data therefrom, control operation of the corresponding device, make operating setting selections for the corresponding device, etc.

In a preferred embodiment, the at least one IoT device 115 is a beacon (i.e., a small, wireless sensor that is integrated in client device). The beacon may include Bluetooth Low Energy (e.g., Bluetooth Smart or Bluetooth Version 4.0+) to broadcast radio signals or to communicate with other smart devices (e.g., other IoT devices and/or client devices 110, 120). The broadcasted beacon signals can be captured by other IoT devices 115 and/or client devices 110, 120, to call ad-hoc actions. In some exemplary embodiments, the beacon may include a GPS tracker.

The beacon may be used for mapping and location services (e.g., a location awareness service or proximity service) using, for example, received signal strength indicator (RSSI) or Wi-Fi access points. The location services may be conducted by a framework (SDK built in the core location), which includes noise reduction algorithms to make the signals smoother and the results fairer.

The at least one GPS tracker 117 may include, for example, an active GPS tracking device (e.g., a receiver) which may provide real-time tracking of a device (e.g., 110 and 120) using a trilateration algorithm. The active GPS tracking device collects data (e.g., location information such as geographic coordinates) from a device (e.g., 110, 115, 120) and sends the data to a central tracking system (e.g., ECMEP 160) for further processing.

Further, each client device (i.e., 110 and 120) may include program code (e.g., App 119), program data, at least one random access memory (RAM), at least one non-volatile memory and at least one microprocessors 113. The program code and/or data may be loaded into the RAM from the non-volatile memory and provided to the at least one microprocessors for execution. The at least one microprocessors can generate and store results in RAM or non-volatile memory for subsequent access, display, output and/or transmission. The program code (e.g., App 119) may comprise multiple hardware or software modules, discussed hereinafter. Further, the program code may contain computer executable instructions that cause the at least one microprocessor to perform a variety of specific tasks, such as, for example, send an emergency alert to the ECMEP, collect data from a corresponding client device (110, 120) and/or IoT device 115, transmit collected data to ECMEP, transmit location data to ECMEP, etc.

The at least one affiliate server 170 is communicably coupled to network 140, and may be implemented as multiple instances wherein the multiple instances may be a joined redundant network or may be singular in nature. Furthermore, the server 170 may be connected to a database. The at least one affiliate service 170 may include at least one or more of a private corporate enterprise, a federal network enterprise, or a statewide network enterprise (e.g., 911 emergency dispatch enterprise). Each enterprise may include one or more microprocessors, one or more memory devices (e.g., random access memory (RAM), non-volatile secondary storage, hard drive, a floppy drive, and a CD-ROM drive), and network interfaces (e.g., a wired or wireless Ethernet card and a digital and/or analog input/output card) and one or more databases. The affiliate server 170 may store any data needed by architecture 100.

Figure 2:
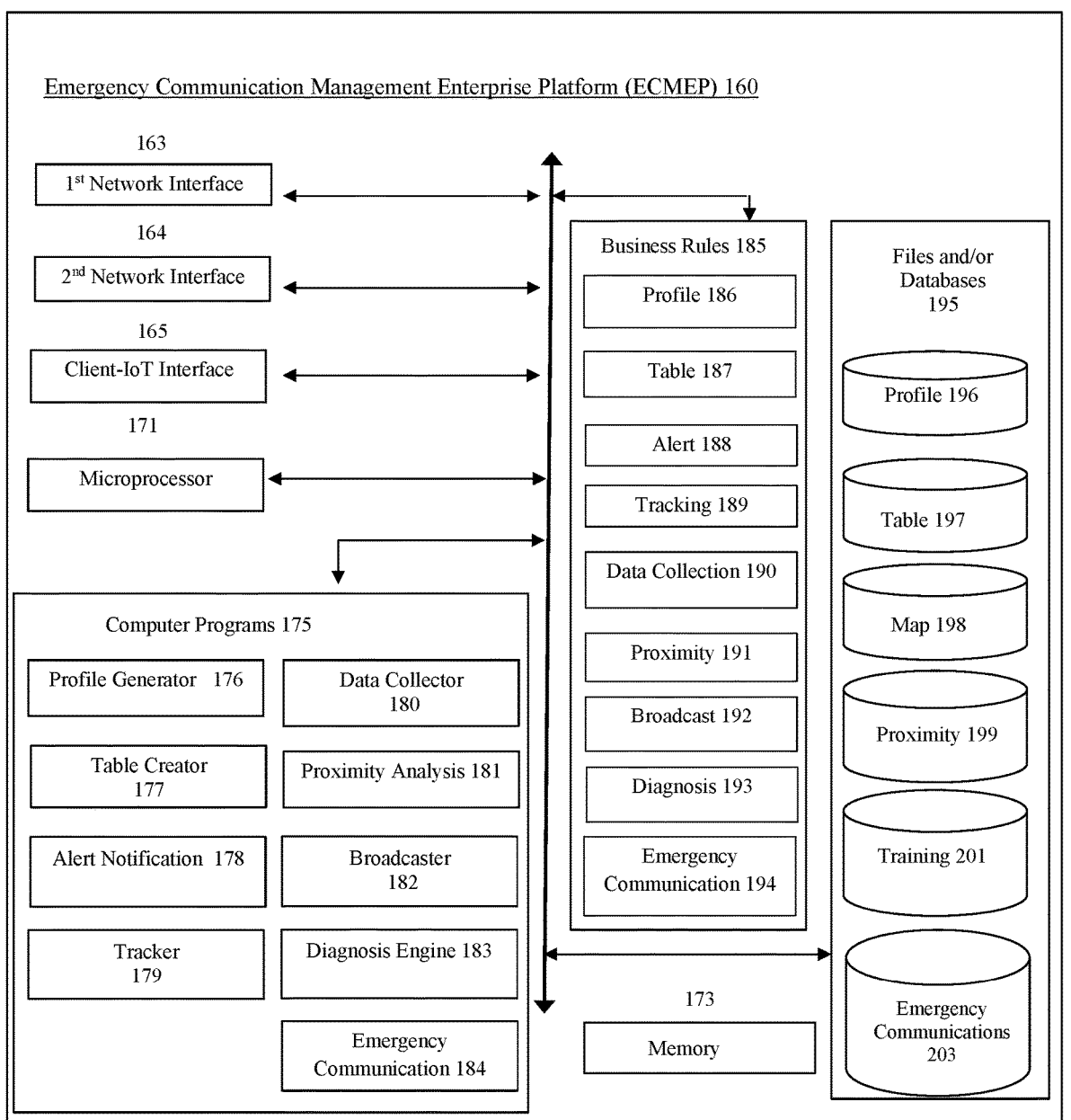
FIG. 2 shows an exemplary view of an emergency communication management enterprise platform (ECMEP) according to an embodiment of the present disclosure.

Referring to FIG. 2, a block diagram illustrating an exemplary emergency communication management enterprise platform ("ECMEP") 160 is shown. The ECMEP may be configured with one or more servers, distributed computing systems, and/or cloud-based computer systems. The ECMEP may include a first network interface 163, a second network interface 164, a client-IoT interface 165, at least one microprocessor 171, and memory 173 which stores computer programs 175 comprising a collection of software modules 176, 177, 178, 179, 180, 181, 182, 183 and 184, a set of business rules 185 comprising 186, 187, 188, 189, 190, 191, 192, 193 and 194, and a plurality of files and/or databases 195 comprising 196, 197, 198, 199, 201 and 203.

Memory 173 may include, for example, any suitable type of memory unit, memory device, memory article, memory medium, storage device, data storage device, storage article, storage medium and/or storage unit, for example, memory, removable or non-removable media, erasable or non-erasable media, writeable or re-writeable media, digital or analog media, hard disk, floppy disk, random access memory (RAM), non-volatile secondary storage, non-volatile storage, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like.

ECMEP 160 may receive inputs from network interfaces 163 and 164 and from Client-IoT interface 165 via network 140. As processing is performed in the ECMEP 160, outputs, such as, for example, real-time broadcast data and emergency communications may be provided to client device (110, 120) and affiliate server 170 via network 140. Network interfaces (e.g., a wired or wireless Ethernet card and a digital and/or analog input/output card), such as, for example, 163 and 164 may be provided to establish a connection to client device (110, 120) and affiliate server 170. The network interfaces may also provide connectivity to other remote entities (e.g., terminals, remote computer systems) that wish to access, interact and/or operate the ECMEP.

Program code, such as the code (i.e., microprocessor/computer executable instructions), comprised in computer programs 175, and program data, such as business rules 185, can be loaded into a RAM from a non-volatile secondary storage and provided to the microprocessor 171 for execution. The microprocessor 171 can generate and store results on a data storage device for subsequent access, display, output and/or transmission to other computer systems and computer programs.

The computer programs 175, which may comprise multiple hardware or software modules, discussed hereinafter, contain program instructions that cause the microprocessor 171 to perform a variety of specific tasks required to parse, extract, index and tag data contained in the databases stored in memory 173. Additionally, the program instructions cause the microprocessor to store data in memory 173. These software modules are flexible, and may be configured to use a large variety of different business rules, including without limitation, profile 186, table 187, alert 188, tracking 189, data collection 190, proximity 191, broadcast 192, diagnosis 193, and emergency communication 194. The purpose and function of each one of the computer software modules in the computer programs 117 will now be described in more detail below.

The computer programs 175 contain program instructions that are converted to executable code. The executable code is committed to memory using machine codes selected from the specific machine language instruction set, or native instructions, designed into the hardware microprocessor. The hardware microprocessor is configured to perform a predefined set of logic operations in response to receiving a corresponding basic instruction selected from a predefined native instruction set of machine codes. Each native instruction is a discrete code that is recognized by the hardware microprocessor and that can specify particular registers for arithmetic, addressing, or control functions; particular memory locations or offsets; and particular addressing modes used to interpret operands. The program instructions are a set of machine codes selected from the native instruction set that are processed by the hardware microprocessor.

The profile generator module 176 in the computer programs 175 contains instructions that when executed by the microprocessor 171, cause the microprocessor to generate a profile for a user of the TEAP and store any received data associated with the user in the user's profile in profile database 196. The profile generator module 118 receives a new user registration request from at least one of requesting client device 110 and affiliate client device 120. The profile generator module generates a profile for the user and stores the profile in the profile database 196. The generated profile may include a user role for each registrant. A user role may include a requester/bystander, an affiliate/responder or an payer). After the profile is generated for the user, the profile generator module may continue to receive data associated with the user from at least one of requesting client device 110 and affiliate client device 120. The profile generator reads the received data and stores the contents in the appropriate field of the user's profile. The profile business rules 186 are used to generate the user's profile and to process and store received data.

A user of the TEAP may include an individual requesting emergency assistance ("requesting user"), such as, for example, a bystander on the scene of an emergency situation (e.g., an individual experiencing a morbidity such as, for example, a drug overdose), a wearable device worn by an individual, or an individual trained to provide immediate lifesaving care (i.e., emergency assistance) to a requesting user ("affiliate user"). In some aspects, a requesting user may include the injured/distressed individual. Each affiliate user is certified as a first responder on the TEAP. The affiliate user is a registered user of the TEAP and is registered as a certified first responder for the TEAP. Each user may register a corresponding client device (110, 120) which is stored in the user's profile.

The table creator module 177 in the computer programs 175 contains instructions that when executed by the microprocessor 171, cause the microprocessor to create a table 197 which lists all TEAP registered affiliate users and their corresponding registered affiliate client device 120. When each affiliate user registers as a user, each affiliate user is required to register an affiliate client device 120 which includes a GPS tracker 117 and an IOT device 115 (e.g., a beacon). The TEAP communicates with the affiliate user by way of the registered affiliate client device. The table creator module 177 uses business rules 187 to create the table and the table is stored in table database 197.

The alert notification module 178 in the computer programs 175 contains instructions that when executed by the microprocessor 171, cause the microprocessor to receive an emergency assistance request from a requesting client device 110 and to send an alert notification to tracker 179, proximity analysis 181 and broadcaster 182. The alert notification module 178 uses business rules 188 to process the emergency assistance request and send an alert notification (i.e., emergency alert) to tracker 179, proximity analysis 181 and broadcaster 182. The alert notification includes the registered requesting client device 110 for the requesting user. In some aspects, the alert notification module sends an emergency notification to the at least one affiliate server 170.

The tracker module 179 in the computer programs 175 contains instructions that when executed by the microprocessor 171, cause the microprocessor to obtain, upon receiving an alert notification from alert notification 178, real-time tracking information from the registered requesting device 110 corresponding to the alert notification continuously during an active emergency assistance pending period (i.e., the requesting client device's location is tracked until the request is completed). Each requesting client device 110 includes a GPS tracker 117 which sends geographic coordinates (e.g., geo-location data) to tracker 179. The tracker module 179 uses business rules 189 to process the geo-location data. The geo-location data may be stored in memory 173 and continuously updated therein. Upon request, the tracker module 179 provides the current geo-location data to proximity analysis 181.

The data collector module 180 in the computer programs 175 contains instructions that when executed by the microprocessor 171, cause the microprocessor to continuously receive tracking (i.e., geo-location) and proximity information from each registered affiliate client device 120 on the TEAP. Each registered affiliate client device 120 includes a GPS tracker 117 which may send geographic coordinates (e.g., geo-location data) to data collector 180 and a IoT device 115 (e.g., a beacon) which may send proximity data (e.g., proximity beacon sensor data, Wi-Fi access points, etc.) to data collector 180.

The data collector module 180 uses business rules 190 and 191 to process the geo-location data and the proximity data respectively. The geo-location and proximity data may be stored in memory 173 and continuously updated therein. Upon request, the data collector module 180 provides geo-location and proximity data for all of the registered affiliated client devices 120 to proximity analysis 181.

In some aspects, the data collector 180 uses data collector business rules 190 and 191 to send current geo-location and proximity data for all of the registered affiliated client devices 120 which are, based on the geo-location data, located in a particular geographic region (e.g., the same geographical region as the requesting client device 110 corresponding to the emergency assistance request) during an active emergency assistance pending period for a corresponding emergency assistance request. A geographical region can include a state, city, county, province, territory, prefectures, etc.

The proximity analysis module 181 in the computer programs 175 contains instructions that when executed by the microprocessor 171, cause the microprocessor to receive geo-location data for a requesting device 110 from tracker 179 and geo-location and proximity data from each registered affiliate client device 120 on the TEAP from data collector 180, perform a proximity analysis using the geo-location data for the requesting device 110, the geo-location and proximity data for each registered affiliate client device 120 in table 197, and map data (e.g., Google Maps or map database 198) to identify at least one affiliate client device within a predetermined distance of the requesting device 110 corresponding to the received alert notification. The identified at least one affiliate client device 120 may be stored in proximity database 199.

In some aspects, the proximity analysis module 181 perform a proximity analysis using the geo-location data for the requesting device 110, the geo-location and proximity data for each registered affiliate client device 120 in table 197, and map data (e.g., Google Maps or map database 198) to identify all of the affiliate client devices 120 listed in table 197 which are located within a predetermined distance of the requesting device 110 corresponding to the received alert notification. The identified affiliate client devices 120 may be stored in proximity database 199.

In some aspects, the proximity analysis module 181 perform a proximity analysis using the geo-location data for the requesting device 110, the geo-location and proximity data for each registered affiliate client device 120 in table 197, and map data (e.g., Google Maps or map database 198) to identify all of the affiliate client devices 120 listed in table 197, that are located in a particular geographic region, which are located within a predetermined distance of the requesting device 110 corresponding to the received alert notification. The identified affiliate client devices 120 may be stored in proximity database 199.

Map database 198 stores a collection of data which is compiled and formatted into a virtual image. The collection of data produces maps that give accurate representations of a particular geographical area, detailing major road arteries and other points of interest.

The analysis performed by the proximity analysis module 181 may include short range proximity detection between the requesting client device 110 and the at least one affiliate client device 120. In some aspects, the analysis performed by the proximity analysis module may include short range proximity detection between the requesting client device and all of the affiliate client devices listed in table 187. In some aspects, the analysis performed by the proximity analysis module 181 may include short range proximity detection between the requesting client device 110 and all of the identified affiliate client devices 120 listed in table 187 which are located in a particular geographic region.

The broadcaster module 182 in the computer programs 175 contains instructions that when executed by the microprocessor 171, cause the microprocessor to broadcast an emergency notification to the at least one identified affiliate client device 120 which is located within a predetermined distance of the requesting device 110. The broadcaster module uses broadcast rules 192 to broadcast the emergency notification. In some aspects, the broadcaster module sends an emergency notification to the at least one affiliate server 170.

The emergency notification is intended to alert certified TEAP first responders that a nearby (i.e., within a predetermined distance) individual (e.g., a bystander or an injured/distressed individual) is in imminent need of medical assistance. The emergency notification may be a push notification which is sent to an affiliate client device. The emergency notification includes the location of the requesting client device. In some aspects, the emergency notification may be a text, short message service (SMS), email, or any other form of communication to alert an affiliate user. An affiliate user may respond to the emergency notification using the TEAP by sending an accept notification thereto. The accept notification allows the TEAP to alert the other identified affiliate users that the emergency is being attended to by another affiliate user.

In some aspects, the broadcaster module 182 contains instructions that when executed by the microprocessor 171, cause the microprocessor to broadcast an emergency notification to all of the affiliate client devices 120 listed in table 197 which are located within a predetermined distance of the requesting device.

In some aspects, the broadcaster module 182 contains instructions that when executed by the microprocessor 171, cause the microprocessor to broadcast an emergency notification to all of the affiliate client devices 120 listed in table 197, that are located in a particular geographic region, which are located within a predetermined distance of the requesting device 110.

The diagnosis engine 183 in the computer programs 175 contains instructions that when executed by the microprocessor 171, cause the microprocessor to confirm whether the individual for whom the requesting user requested assistance is in fact injured/distressed. In some aspects, the diagnosis engine may receive on the scene data captured from an affiliate client device 120 and analyze the data using the diagnosis business rules 193 to confirm whether the individual that the requesting user requested assistance for is in fact injured/distressed.

In some aspects, the diagnosis engine 183 may include artificial intelligent computer vision features to auto-recognize human behaviors exhibiting a morbidity from data captured from an affiliate client device with capabilities to capture computer vision data (e.g., from augmented reality (AR) goggles). In this instance, the diagnosis engine uses the data in training database 201 and the diagnosis business rules 193 to confirm whether the individual for whom the requesting user requested assistance is in fact injured/distressed.

The emergency communication module 184 in the computer programs 175 contains instructions that when executed by the microprocessor 171, cause the microprocessor to send instructional steps to the affiliate client device 120 using the emergency communication business rules 194 and data stored in emergency communications database 203. The instructional steps are the steps an affiliate user shall administer to provide aid to the injured/distressed individual. The emergency communication may be provided as voice instructions or displayed as text instructions on a user interface. As noted above, the affiliate client device may be a mobile device, in which case, the emergency communication is sent to the mobile device. In some aspects, the affiliate client device may be a wearable augmented reality head mounted display, in which case, the emergency communication is sent to the wearable augmented reality head mounted display. In other aspects, the affiliate client device may be a wrist-worn wearable, in which case, the emergency communication is sent to the wrist-worn wearable as a holographic image.

FIG. 3 shows an exemplary flow diagrams (i.e., 300, 400) illustrating, by way of example, the steps performed in the TEAP (including back-end ECMEP 160) that may be implemented in accordance with certain embodiments of the present disclosure. The exemplary flow diagrams illustrate a sequence of operations that can be implemented in hardware, software, or a combination thereof. In the context of software, the operations represent computer-executable instructions stored on one or more non-transitory computer-readable media that when executed by one or more processors, perform the recited operations. Generally, computer-executable instructions include routines, programs, objects, components, data structures, and the like that perform particular functions or implement particular abstract data types.

The order in which the operations are described is not intended to be construed as a limitation, and any number of the described operations may be carried out in a different order, omitted, combined in any order, and/or carried out in parallel.

Turning to FIG. 3, at step 310, an emergency assistance request is received (performed by alert notification module 178) from at least one requesting client device 110. At step 320, at least one affiliate client device 120 within a predetermined distance of the requesting client device is identified upon receipt of an emergency assistance request (described in FIG. 4). At step 330, an emergency alert notification (i.e., emergency notification) is broadcast to the at least one affiliate client device 120 identified within a predetermined distance of the requesting device (performed by broadcaster module 182). At step 340, the emergency is confirmed by the ECMEP (performed by diagnosis engine 183) and upon confirmation of the emergency an emergency communication is sent to the at least one affiliate client device at step 350 (performed by emergency communication module 184).

Turning to FIG. 4, the exemplary steps performed when identifying at least one client device within a predetermined distance of the requesting client device is disclosed. At step 410, location data for the requesting client device 110 is received (by tracker module 179) and at step 420 the location of the requesting client device 110 is tracked (performed by tracker module 179). At step 430, the table of affiliated client device (created by table creator module 177) and the location and proximity data collected by the data collector module 180 is accessed to perform the proximity analysis at step 440 (performed by proximity analysis module 181) to identify at least one affiliate client device within a predetermined distance (nearby) of the requesting client device 110 (i.e., step 450)

As noted above, the order of processing of the steps illustrated in the flow diagrams in FIGS. 3-4, may be carried out in a different order, omitted, combined in any order, and/or carried out in parallel.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component.

Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

Blocks of the block diagrams and flow diagrams support combinations of means for performing the specified functions, combinations of elements or steps for performing the specified functions, and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Any memory device may incorporate electronic, magnetic, optical, and/or other types of storage media. In the context of this document, a "non-transitory computer-readable medium" can be, for example but not limited to, an electronic, magnetic, optical, electromagnetic, infrared, or semiconductor system, apparatus, or device. More specific examples (a non-exhaustive list) of the computer-readable medium would include the following: a portable computer diskette (magnetic), a random access memory (RAM) (electronic), a read-only memory (ROM) (electronic), an erasable programmable read-only memory (EPROM, EEPROM, or Flash memory) (electronic), and a portable compact disc read-only memory (CD ROM) (optical).

The terms "module' and "component as used herein generally represent Software, firmware, hardware, or combinations thereof. In the case of a software implementation, the module or component represents program code that performs specified tasks when executed on a processor. The program code may be stored in one or more computer readable memory devices.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions or a computer program product stored on one or more computer-readable storage media and executed on a computing device (e.g., any available computing device, including smart phones or other mobile devices that include computing hardware). Computer-readable storage media are any available tangible media that can be accessed within a computing environment (e.g., one or more optical media discs such as DVD or CD, volatile memory components (such as DRAM or SRAM), or nonvolatile memory components (such as flash memory or hard drives)). The term computer-readable storage media does not include signals and carrier waves. In addition, the term computer-readable storage media does not include communication connections.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, or any other suitable programming language. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Embodiments according to the disclosure are in particular disclosed in the attached claims directed to a method, a storage medium, a device and a computer program product, wherein any feature mentioned in one claim category, e.g., method, can be claimed in another claim category, e.g., system, as well. The dependencies or references back in the attached claims are chosen for formal reasons only. However, any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

The foregoing description of one or more implementations provides illustration and description, but is not intended to be exhaustive or to limit the scope of embodiments to the precise form disclosed. Modifications and variations are possible in light of the above teachings or may be acquired from practice of various embodiments.

What is claimed is:

1. A computer implemented method of detecting and processing emergency communications in real-time using an emergency communication management enterprise platform ("ECMEP"), the computer implemented method comprising steps of:

receiving, by the ECMEP, an emergency assistance request from a requesting client device;

automatically tracking, by the ECMEP, geographic coordinates of the requesting client device; device;

performing, by the ECMEP, a proximity analysis to identify at least one affiliate client device within a predetermined distance of the requesting client device upon receipt of an emergency assistance request;

broadcasting, by the ECMEP, an emergency notification to the identified at least one affiliate client device within the predetermined distance of the requesting client device;

processing, by the ECMEP, computer vision data received from the at least one affiliate client device having computer vision capture capabilities, wherein the ECMEP includes artificial intelligence features configured to auto-recognize human behaviors exhibiting a morbidity based on data stored in a training database and applied diagnosis business rules, and to confirm whether an individual associated with the requesting client device is injured or distressed; and broadcasting, by the ECMEP, an emergency notification and instructional steps to the identified at least one affiliate client device, wherein the ECMEP transmits the instructional steps in a format corresponding to the affiliate client device type, including voice instructions, text-based instructions, or holographic or augmented reality (AR) visual instructions displayed through a wearable AR head-mounted display or body-worn wearable device.

2. The computer implemented method of claim 1, further comprising transmitting, by the ECMEP, an emergency notification to an affiliate server upon receipt of the emergency assistance request.

3. The computer implemented method of claim 1, further comprising creating, by the ECMEP, a table including a list of affiliate client devices.

4. The computer implemented method of claim 3, further comprising continuously collecting, by the ECMEP, geo-location and proximity data from the list of affiliate client devices.

5. The computer implemented method of claim 4, further comprising identifying from the list of affiliate client devices, all of the affiliate devices within the predetermined distance of the requesting device.

6. The computer implemented method of claim 5, further comprising broadcasting the emergency notification to all of the identified affiliate devices within the predetermined distance of the requesting device.

7. The computer implemented method of claim 4, wherein the proximity data includes proximity beacon sensor data.

8. The computer implemented method of claim 4, wherein the proximity data includes Wi-Fi access points data.

9. The computer implemented method of claim 1, wherein the performed proximity analysis includes short range proximity detection between the requesting client and the at least one affiliate client device.

10. The computer implemented method of claim 1, further comprising performing, by the ECMEP, diagnosis analytics on information received from an affiliate client device to confirm an emergency.

11. The computer implemented method of claim 10, further comprising transmitting, by the ECMEP, an emergency communication to the affiliate client device upon confirmation of the emergency.

12. The telehealth system of claim 10, wherein the server further comprises a first network interface configured to transmit an emergency notification to an affiliate server.

13. The telehealth system of claim 10, wherein the server further comprises a second network interface configured to continuously collect location data from the list of affiliate client devices.

14. The telehealth system of claim 10, wherein the server further comprises a machine learning module including at least one processor configured to execute computer executable instructions to:

perform diagnosis analytics on information received from an affiliate client device using at least one machine learning algorithm to confirm an emergency.

15. The telehealth system of claim 14, wherein the server further comprises a third network interface for transmitting an emergency communication to the affiliate client device upon confirmation of the emergency.

16. The telehealth system of claim 10, wherein the performed proximity analysis includes short range proximity detection between the requesting client and the at least one affiliate client device.

17. A telehealth system for detecting and processing emergency communications in real-time, the telehealth system comprising:
  at least one client;

a server including:
a client-IoT interface for interfacing with the at least one client;
at least one data storage device including a first database for storing a list of affiliate client devices;
at least one microprocessor and memory storing executable instructions that, when executed, cause the server to:
  receive an emergency assistance request from a requesting client device;
automatically track the geographic coordinates of the requesting client device;
  perform a proximity analysis to identify at least one affiliate client device within a predetermined distance of the requesting client device upon receipt of the emergency assistance request;
  broadcast an emergency notification to the at least one affiliate client device within the predetermined distance of the requesting client device;
  process computer vision data received from the at least one affiliate client device having computer vision capture capabilities;
  auto-recognize human behaviors exhibiting a morbidity based on data stored in a training database and applied diagnosis business rules;
  confirm whether an individual associated with the requesting client device is injured or distressed; and
  broadcast an emergency notification and instructional steps to the identified at least one affiliate client device;
  wherein the instructional steps are transmitted in a format corresponding to the affiliate client device type, including voice instructions, text-based instructions, or holographic or augmented reality (AR) visual instructions displayed through a wearable AR head-mounted display or body-worn wearable device.

18. A non-transitory computer readable medium comprising instructions, that when executed by a processor, cause the processor to perform:
  receive an emergency assistance request from a requesting client device;
  automatically track the geographic coordinates of the requesting client device;
  perform a proximity analysis to identify at least one affiliate client device within a predetermined distance of the requesting client device upon receipt of the emergency assistance request;
  broadcast an emergency notification to the at least one affiliate client device within the predetermined distance of the requesting client device;
  process computer vision data received from the at least one affiliate client device having computer vision capture capabilities;
  auto-recognize human behaviors exhibiting a morbidity based on data stored in a training database and applied diagnosis business rules;
  confirm whether an individual associated with the requesting client device is injured or distressed; and
  broadcast an emergency notification and instructional steps to the identified at least one affiliate client device;
  wherein the instructional steps are transmitted in a format corresponding to the affiliate client device type, including voice instructions, text-based instructions, or holographic or augmented reality (AR) visual instructions displayed through a wearable AR head-mounted display or body-worn wearable device.

19. The non-transitory computer readable medium of claim 18, wherein the instructions, when executed by the processor, further cause the processor to:

create a table including a list of affiliate client devices; and continuously collect location data from the list of affiliate client devices.

20. The non-transitory computer readable medium of claim 19, wherein the instructions, when executed by the processor, further cause the processor to:

perform diagnosis analytics on information received from an affiliate client device to confirm an emergency; and transmit an emergency communication to the affiliate client device upon confirmation of the emergency.

\* \* \* \* \*